(12) United States Patent
Raymond et al.

(10) Patent No.: US 6,613,532 B1
(45) Date of Patent: Sep. 2, 2003

(54) ANTI-LAMIN ANTIBODIES, ENDOGENEOUS INHIBITORS OF THROMBOSIS

(75) Inventors: Yves Raymond, Longueuil (CA); Jean-Luc Senécal, Outremont (CA)

(73) Assignee: Université de Montreal, Montréal (CA)

( * ) Notice: Subject to any disclaimer, the term of this patent is extended or adjusted under 35 U.S.C. 154(b) by 0 days.

(21) Appl. No.: 09/890,263

(22) PCT Filed: Feb. 9, 2000

(86) PCT No.: PCT/CA00/00116
§ 371 (c)(1),
(2), (4) Date: Nov. 7, 2001

(87) PCT Pub. No.: WO00/47997
PCT Pub. Date: Aug. 17, 2000

Related U.S. Application Data

(60) Provisional application No. 60/119,583, filed on Feb. 10, 1999.

(51) Int. Cl.[7] ............ G01N 33/53; A61K 38/16; A61K 35/14; C12P 21/08
(52) U.S. Cl. ............ 435/7.1; 530/358; 530/380; 530/388.25
(58) Field of Search ............ 435/7.1; 530/300, 530/358, 381, 387.1, 388.25, 380

(56) References Cited

PUBLICATIONS

Luzzana C, Gerosa M, Riboldi P, Meroni PL. Up–date on the antiophospholipid syndrome. J Nephrol.;15(4):342–8, 2002.*

Papmarcaki T, Kouklis PD Kreis TE, Georgatos SD. The "lamin B–fold". Anti–idiotypic antibodies reveal a structural complementarity between nuclear lamin B and cytoplasmi-cintermediate filament epitopes. J Biol Chem. 1991 Nov. 5;266(31):21247–5.*

Pollard KM et al., Mol Cel Biol 1990; 10:2164–2175.

Heitlinger E et al., J Cell Biol 1991; 113: 485–495.

Gagnon G et al., Bio Rad US/EG Bulletin 1992; 1773.

Senecal et al., Arthritis & Rheumatism 1999; 42: 1347–1353.

Hill et al., Australian and New Zealand Journal of Medicine 1996, 26:162–166.

Uthman et al., Clinical and Investigative Medicine 1994, 17: B127.

Mariette et al., Arthristis and Rheumatism 1993, 36: 1315–1324.

Lassoued et al., Annals of Internal Medicine 1988, 108:829–833.

Guilly et al., European Journal of Cell Biology 1987, 43:266–272.

Guilly et al., Immunobiology 1986, 173:330–331.

* cited by examiner

Primary Examiner—Christina Chan
Assistant Examiner—Maher Haddad
(74) Attorney, Agent, or Firm—Ogilvy Renault France Côté

(57) ABSTRACT

The present invention relates to a method to determine predisposition to coagulation disorders, such as thrombosis, to a method for diagnosis of lupus, and therapeutical uses thereof in the treatment of coagulation disorders. More specifically, the present invention relates to a method to determine predisposition to coagulation disorders in a patient, which comprises the step of determining the presence or absence of anti-lamin B1 (aLB1) antibodies and of lupus anticoagulant (LA) antibodies; and wherein presence of aLB1 and LA antibodies is indicative of a low risk of coagulation disorders incidence

3 Claims, 2 Drawing Sheets

ANTI-LAMIN ANTIBODIES, ENDOGENEOUS INHIBITORS OF THROMBOSIS

This application claims the benefit of provisional application Ser. No. 60/119,583 filed Feb. 10, 1999.

BACKGROUND OF THE INVENTION (a) Field of the Invention

The invention relates to a method to determine predisposition to coagulation disorders, such as thrombosis, to a method for the diagnosis of lupus, and method of treatment of coagulation disorders.

(b) Description of Prior Art

The major causes of acquired coagulation disorders are (1) vitamin K deficiency, (2) liver disease, (3) disseminated intravascular coagulation (DIC), and (4) development of circulating anticoagulants, which are usually antibodies (Abs) to hemostatic factors.

DIC usually results from entrance into or generation within the blood of material with tissue factor activity (TFA), which initiates coagulation. DIC usually arises in 1 of 3 clinical circumstances: (1) In complications of obstetrics, uterine material with TFA gains access to the maternal circulation (eg, in abruptio placentae, a saline-induced therapeutic abortion, retained dead fetus syndrome, and the initial phase of amniotic fluid embolism). (2) Infection is present, particularly with gram-negative organisms. Adding gram-negative endotoxin to blood in vitro causes generation of TFA on the plasma membrane of monocytes. This presumably represents a primary mechanism for endotoxin-induced DIC, since depletion of blood monocytes in rabbits by giving the alkylating agent nitrogen mustard protects the animals from developing DIC after injection of endotoxin. (3) Malignancy is present, particularly mucin-secreting adenocarcinomas of the pancreas and prostate and a form of acute leukemia, acute promyelocytic leukemia, in which hypergranular leukemic cells are thought to release material from their granules with TFA.

The guiding principle of therapy is to identify and correct the underlying cause without delay (eg, broad-spectrum antibiotic treatment of suspected gram-negative sepsis, evacuation of the uterus in abruptio placentae). Once this is accomplished, DIC should subside quickly. If the patient is bleeding seriously, replacement therapy is indicated: platelet concentrates to correct thrombocytopenia (and also as a source of factor V in platelets); cryo-precipitate to replace fibrinogen and factor VIII; fresh frozen plasma to increase levels of factor V, other clotting factors, and as a source of antithrombin III, which may also be depleted secondary to DIC.

Endogenous substances that inhibit blood coagulation are usually antibodies (Abs) that neutralize a clotting factor activity (eg, an Ab against factor VIII or factor V) or the activity of the procoagulant phospholipid used in certain coagulation test systems (the lupus anticoagulant). Rarely, circulating anticoagulants are not Abs but glycosaminoglycans with heparin-like anticoagulant activity arising from their ability to increase antithrombin III reactivity. These heparin-like anticoagulants are found mainly in patients with multiple myeloma or other hematologic malignancies.

Occasionally, Abs are not circulating anticoagulants, since they do not neutralize a clotting factor activity. These Abs usually cause bleeding by binding prothrombin. Although the prothrombin-antiprothrombin complex retains its coagulant activity in vitro, it is rapidly cleared from the blood in vivo, with resultant acute hypoprothrombinemia.

A common anticoagulant first described in patients with SLE was logically called the lupus anticoagulant; subsequently it was recognized in patients with a variety of disorders, often as an unrelated finding. The phenomenon of anticoagulation results when Abs react with epitopes on anionic phospholipids (including the phospholipids used in the PTT and in specific clotting factor assays based upon the PTT technique). The following pattern of test results is found: a prolonged PTT that fails to correct with a 1:1 mixture of the patient's and normal plasma, a normal or minimally prolonged PT, and a nonspecific depression of those clotting factors measured by a PTT technique (factors XII, XI, IX and VIII). Some patients will also have a false-positive VDRL test for syphilis, in which the phospholipid cardiolipin is used as the antigen, and most patients will have evidence of Abs reacting with cardiolipin by a more sensitive radioimmunoassay technique.

Although the anticoagulant interferes with the function of procoagulant phospholipid in clotting tests in vitro, patients with only the lupus anticoagulant do not bleed excessively. Apparently, the anticoagulant does not interfere with the function of procoagulant phospholipid on cell surfaces in vivo. Paradoxically, however, for an unknown reason, patients with the lupus anticoagulant are at increased risk for thrombosis, which may be either venous or arterial. If such a patient experiences a thrombotic episode, long-term prophylaxis with anticoagulant therapy should be seriously considered. Repeated abortions in the first trimester, possibly related to thrombosis of placental vessels, have also been reported occasionally.

A subset of patients with the lupus anticoagulant develop a second Ab, which was described earlier the non-neutralizing Ab to prothrombin that induces hypoprothrombinemia and these patients do bleed abnormally. Hypoprothrombinemia is suspected when the screening tests reveal a long PT in addition to the long PTT and is confirmed by a specific assay. Treatment with corticosteroids is indicated; usually the PT returns rapidly to normal and bleeding is controlled.

Hepatic artery occlusion is uncommon but can be caused by thrombosis, embolism, abdominal trauma or surgical ligation. The occlusion may produce an ischemic infarct of the liver, but results are unpredictable because of individual differences in hepatic vasculature and the extent of collateral circulation.

Previous studies have reported autoantibodies to nuclear lamin B1 in a small number of selected SLE patients. However, the clinical associations of anti-lamin B1 are unclear.

To date there exist no diagnosis test for the clinical predisposition and/or prognosis of coagulation disorders, such as thrombosis.

It would be highly desirable to know the distribution, the titer and the clinical significance of high titers of IgG anti-lamin B1 autoantibodies in a large number of unselected and well-characterized SLE patients, disease controls and normal controls.

SUMMARY OF THE INVENTION

One aim of the present invention is to provide the clinical significance of high titers of IgG anti-lamin B1 autoantibodies in a subset of SLE patients, disease controls and normal controls.

In accordance with an embodiment of the present invention there is provided a method to determine predisposition to coagulation disorders in a patient, which comprises the step of determining the presence or absence of anti-lamin B1 (aLB1) antibodies in a biological sample of the patient; wherein absence of aLB1 antibodies is indicative of a predisposition to coagulation disorders; and wherein presence of aLB1 antibodies is indicative of a low risk of coagulation disorders incidence.

The method may further comprises determining the presence or absence of lupus anticoagulant (LA) antibodies in the biological sample; wherein presence of LA and aLB1 antibodies is indicative of a low risk of coagulation disorders incidence; and wherein presence of LA antibodies with absence of aLB1 antibodies is indicative of a predisposition to coagulation disorders.

Such a determining step may be effected with LA and LB1 antigen.

The coagulation disorders include, without limitation, thrombosis.

The biological sample include, without limitation, a serum sample.

In accordance with another embodiment of the present invention there is provided a method for diagnosis of lupus or of non-lupus in a patient, which comprises determining the presence of anti-lamin B1 antibodies (aLB1) in a biological sample of the patient, wherein presence of aLB1 is indicative of a lupus diagnosis.

In accordance with another embodiment of the present invention there is provided a method of treatment of coagulation disorders in a patient, which comprises administering a aLB1 compound which mimics activity of anti-lamin B1 (aLB1) antibodies inhibiting thrombosis.

In accordance with another embodiment of the present invention there is provided the use of a aLB1 compound in the preparation of a medicament for the treatment of coagulation disorders in a patient, wherein the aLB1 compound mimics activity of anti-lamin B1 (aLB1) antibodies inhibiting thrombosis.

In accordance with another embodiment of the present invention there is provided a peptide for the inhibition of coagulation which comprises a peptide directly or indirectly derived from LB1 antibodies, wherein the peptide mimic inhibiting thrombosis activity of anti-lamin B1 (aLB1) antibodies.

DETAILED DESCRIPTION OF THE INVENTION

Figure 1:
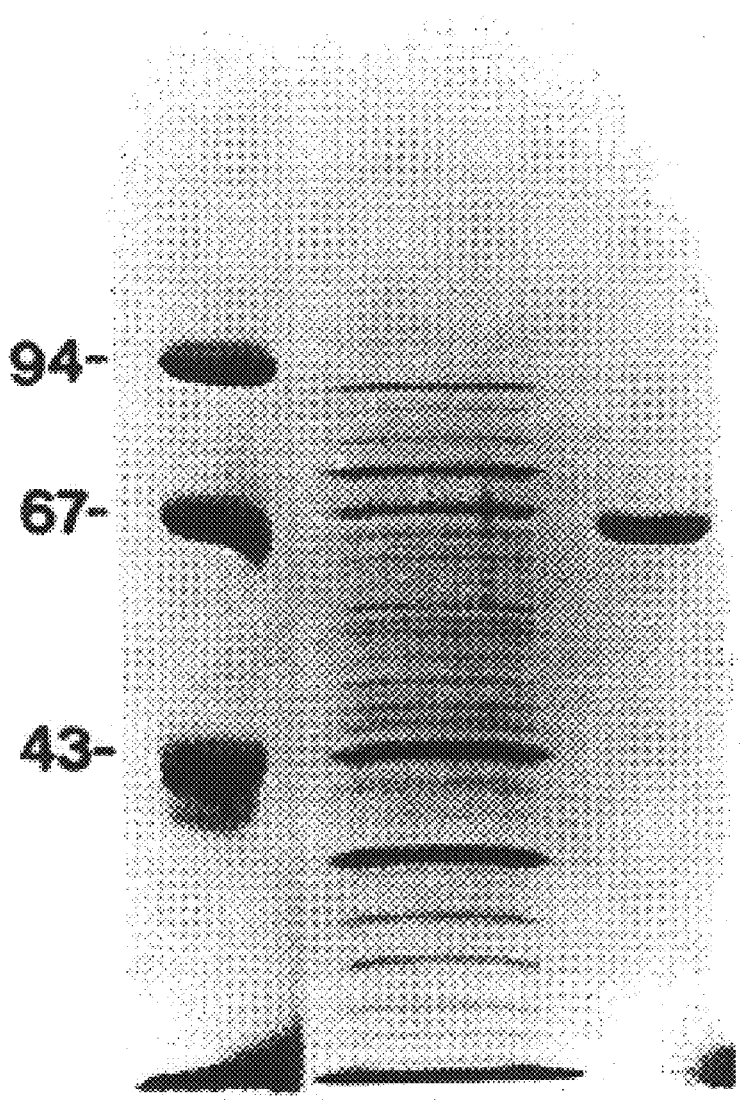
FIG. 1 illustrates recombinant lamin B1 purified from bacterial lysates.

In accordance with the present invention, there is shown that high titers of autoantibodies to nuclear lamin B1 are highly specific for a subset of patients with SLE, characterized by the presence of lupus anticoagulant antibodies (LA). The frequency of thrombosis in SLE patients expressing both LA and anti-lamin B1 autoantibodies was similar to patients without LA. However, patients expressing LA without anti-lamin B1 had a significantly greater frequency of thrombosis. The presence of LA without anti-lamin B1 may define a subset of SLE patients at greater risk for thrombosis.

A cross-sectional study of anti-lamin B1 autoantibodies was performed on frozen serum samples obtained at first evaluation by us of 238 consecutive French Canadian adults: 61 normal controls, 20 osteoarthritis, 22 ankylosing spondylitis, 11 autoimmune hepatitis, 30 RA and 94 SLE patients. SLE patients were studied for 57 disease manifestations. Also a case-control study was performed to analyze the relationship between anti-lamin B1 status and thrombotic manifestations between SLE onset and last followup. IgG anti-lamin B1, as measured by ELISA using human recombinant lamin B1 autoantigen, were considered to be present in high titer if they exceeded 16 SD above the mean in normal controls.

High titers of anti-lamin B1 were strikingly restricted to a subset of 8 (8.5%) SLE patients. The mean anti-lamin B1 titer was higher in this subset than in other SLE patients or any control group ($P<0.001$). By univariate analysis, the most striking association of anti-lamin B1 was with lupus anticoagulant antibodies (LA) (100% versus 18.6%, OR 72.6, 95% CI 3.9 to 1323.8, $P=0.00001$). Other associations of anti-lamin B1 included thrombocytopenia (62.5% versus 19.8%, OR 6.7, 95% CI 1.46 to 31.1, $P=0.016$) and IgG anti-b2-glycoprotein I autoantibodies (75% versus 29.1%, OR 7.3, 95% CI 1.38 to 38.7, $P=0.014$). By stepwise multiple logistic regression, LA was the variable most strongly associated with anti-lamin B1 autoantibodies. Although LA were significantly associated with thrombosis in our SLE patients (OR 3.17, 95% CI 1.4 to 9.5, $P=0.024$), anti-lamin B1 were not. Therefore, we studied the effect of anti-lamin B1 on the frequency of thrombosis in patients with LA. The frequency of thrombosis in SLE patients expressing both LA and anti-lamin B1 was similar to patients without LA (OR 1.179, 95% CI 0.26 to 5.28, $P=1.0$). However, patients expressing LA without anti-lamin B1 had a greater frequency of thrombosis (OR 4.24, 95% CI 1.37 to 13, $P=0.018$)

High titers of IgG anti-lamin B1 autoantibodies are highly specific for a subset of SLE patients characterized by the presence of LA and other laboratory manifestations of the antiphospholipid syndrome. The presence of LA without anti-lamin B1 may define a subset of SLE patients at greater risk for thrombosis.

High titers of autoantibodies to nuclear lamin B1 have been reported in a small number of patients with systemic lupus erythematosus (SLE) or an SLE-like illness. Intriguingly, some of these studies noted the presence of a circulating anticoagulant, thrombocytopenia, anticardiolipin antibodies (aCL), Coombs positive hemolytic anemia and neutropenia in association with high titers of anti-lamin B1 autoantibodies. However, in these reports, patients were selected, based on the peripheral (rim) pattern characteristic of antibodies to nuclear lamin B1 on fluorescent antinuclear antibody testing. In addition, these studies used few normal controls and no rheumatic disease or autoimmune disease controls. Finally, none of these studies used recombinant human lamin B1 autoantigen to measure and to assess the significance of anti-lamin B1 autoantibodies.

Therefore we undertook the present study to determine the frequency and clinical associations of high titers of anti-lamin B1 autoantibodies in a large number of unselected and well-characterized SLE patients. We used recombinant human lamin B1 in a newly developed ELISA to quantitate anti-lamin B1 antibodies in these patients and in a large number of rigorously defined normal and disease controls. Using univariate and multiple regression analyses, we show that a subset of SLE patients express high titers of anti-lamin B1 autoantibodies, and that these antibodies are strikingly associated with lupus anticoagulant antibodies (LA). Furthermore, although the frequency of thrombotic manifestations in patients expressing both LA and high titers of anti-lamin autoantibodies was similar to patients without LA, a significantly greater frequency of thrombosis was observed in patients with LA alone.

PATIENTS AND METHODS

Patients and Controls

A cross-sectional study of IgG anti-lamin B1 was performed on serum samples obtained at the time of first evaluation by us at the Connective Tissue Diseases Clinic and General Rheumatology Clinic (Hôpital Notre-Dame, Centre Hospitalier de l' Université de Montreal). Serum samples were coded and frozen at −80° C. The study population consisted of 238 adults distributed into a normal control group and 5 patient groups (Table 1).

TABLE 1

Demography of 238 adults studied

| GROUP | N | GENDER | N | % | MEAN AGE | | |
|---|---|---|---|---|---|---|---|
| NORMAL CONTROLS | 61 | F | 45 | 73.8 | 46.28 | SD | 15.67 |
| | | M | 16 | 26.2 | 46.91 | SD | 13.23 |
| PRIMARY OSTEOARTHRITIS | 20 | F | 15 | 75 | 73.04 | SD | 7.35 |
| | | M | 5 | 25 | 71.09 | SD | 6.46 |
| ANKYLOSING SPONDYLITIS | 22 | F | 6 | 27.3 | 39.86 | SD | 10.49 |
| | | M | 16 | 72.7 | 41.64 | SD | 13.33 |
| RHEUMATOID ARTHRITIS | 30 | F | 23 | 76.7 | 56.69 | SD | 12.14 |
| | | M | 7 | 23.3 | 58.86 | SD | 9.00 |
| SYSTEMIC LUPUS ERYTHEMATOSUS | 94 | F | 87 | 92.56 | 37.32 | SD | 13.71 |
| | | M | 7 | 7.44 | 40.96 | SD | 13.19 |
| CHRONIC ACTIVE HEPATITIS | 11 | F | 11 | 100 | 44.76 | SD | 18.75 |
| | | M | 0 | 0 | | | |

Inclusion into the normal control group (n=61) required a normal history and physical examination, including the absence of known autoimmune diseases in relatives, as previously described. A higher proportion of women was recruited to respect the higher female prevalence of the autoimmune diseases studied. Patient groups consisted of 20 primary osteoarthritis, 22 ankylosing spondylitis, 30 rheumatoid arthritis (RA), 94 SLE, and 11 autoimmune hepatitis patients evaluated consecutively. Diagnoses for the patient groups were according to the American College of Rheumatology criteria as previously described. Autoimmune hepatitis sera were from Dr. Denis Marleau (André Viallet Clinical Research Center, Hôpital St-Luc, Centre Hospitalier de l' Université de Montréal). The medical records of the 94 SLE patients were reviewed retrospectively using a standardized SLE protocol for the presence of 57 clinical and laboratory manifestations of SLE between disease onset and first evaluation by us. SLE patients and most controls were French Canadians.

Thrombosis and Fetal Loss

This was studied using a case-control design. The charts of the 94 SLE patients were reviewed retrospectively using a standardized vascular protocol for thrombotic and embolic manifestations and fetal loss at any time between disease onset and last followup as previously reported. Among these patients, 8 had deep vein thrombosis, 14 had cerebral infarction, 8 had myocardial infarction, 7 had deceased by coronary artery disease, 13 had other thrombotic events, and 6 had embolic events. Thirty-two patients had one or more of these events. These patients were categorized as those with a history of thrombosis, while all other SLE patients were categorized as patients without such a history. Four patients had fetal loss, defined as 2 or more unexplained first trimester or one or more unexplained second or third trimester loss.

Preparation and Purification of Recombinant Lamin B1

The full length cDNA for human lamin B1 was a kind gift of K. M. Pollard of the Research Institute of Scripps Clinic, La Jolla, Calif. (Pollard KM et al., Mol Cel Biol 1990; 10:2164–2175). The cDNA was inserted into the T7 polymerase-based pET-11d expression vector from Novagen (Madison, Wis.). Transformation was into BL21 (DE3) bacteria for protein expression, following manufacturer's instructions. Lamin B1 was extracted as described for lamin B2 (Heitlinger E et al., J Cell Biol 1991; 113: 485–495). Further purification of lamin B1 was achieved by preparative sodium dodecyl sulfate (SDS)-gel electrophoresis and continuous elution using the Prep Cell apparatus from Bio Rad (Hercules, Calif.), as described (Gagnon G et al., Bio Rad US/EG Bulletin 1992; 1773). The overall yield of purified lamin B1 ranged from 1.5 to 2.0 mg per liter of original bacterial culture. FIG. 1 shows an electrophoretic profile of purified lamin B1 where a single polypeptide is present. An 8% polyacrylamide-SDS gel was loaded with molecular weight markers (lane M), a bacterial lysate sample equivalent to 109 $\mu$l of original bacterial culture (lane 1) and a 2.5 $\mu$g sample of lamin B1 (lane 2) purified as described under Materials and Methods. The gel was stained with Coomassie blue. Molecular masses indicated on the left are in kDa.

Anti-Lamin B1 ELISA

Immulon 2 (gamma-irradiated) ELISA plates (Dynatech, Alexandria, Va.) were coated for 16 hrs with 100 microliters/well of purified lamin B1 diluted to 4 mg/ml in buffer containing 0.28 mM Tris-HCl, pH 7.4, and 0.224 M urea, or with buffer alone to determine the non specific binding of each serum. All incubations were at 25° C. After 4 washes with phosphate buffered saline, pH 7.4 (PBS), containing 0.05% Tween 20 (Sigma, St. Louis, Mo.), the plates were blocked for two hours with 200 microliters/well of PBS containing 2% casein and 10% normal goat serum (NGS; Gibco, Burlington, Ontario) (blocking buffer). After 4 washes, sera diluted 1:100 in blocking buffer were added (100 microliters/well) to duplicate wells and incubated for 1 hour. The plates were washed four times and peroxidase-conjugated goat anti-human IgG (g-chain specific, Jackson ImmunoResearch Laboratories, Baltimore, Md.) diluted 1:5000 in blocking buffer was added (100 microliters/well) and incubated for 1 hour. After 4 washes, 100 microliters/well of 0.4 mg/ml of o-phenylenediamine (Sigma) in 0.1 M citrate buffer, pH 6, containing 0.003% $H_2O_2$, was added and the plates were developed for 10 minutes. The plates were read at 492 nm using an ELISA reader. Each plate included a negative control serum from a normal subject and a positive control serum from an SLE patient. For each serum, the optical density (OD) values of control wells was substracted from the OD obtained on antigen coated wells. Results were calculated as the mean of duplicate values for each serum and were expressed as a percentage of the positive control on that plate.

Criteria for ELISA specificity included reactivity of murine monoclonal anti-lamin B1 antibodies to recombinant human lamin B1, absorption studies, low OD values with normal control sera, and low background OD values obtained in antigen negative wells.

Selection of the Anti-Lamin B1 ELISA Cut-Off Value

The cut-off value for anti-lamin B1 IgG antibodies was based on the mean and standard deviation of the normal subjects. From previous immunoblotting and indirect immunofluorescence studies, we expected a bi-modal distribution of anti-lamin B1 autoantibodies in SLE patients but not in other groups, with a first SLE subset expressing lower titers overlapping with several diseases, and a second SLE subset expressing high titers highly restricted to SLE patients. We defined the cut-off point for high-titer anti-lamin B1 as the value correlating with immunofluorescence and immunoblotting results.

Detection of Anti-b2-Glycoprotein I Antibodies (Anti-b2gpI)

ELISA plates were coated with 50 microliters/well of 10 mg/ml human b2gpI (PerImmune Inc., Rockville, Md.) or, as a control, with 50 microliters/well of 10 mg/ml of blocking buffer, in 0.05 M carbonate/bicarbonate buffer, pH 9.6, for 16 hrs at 4° C. All further incubations were at 25° C. After 4 washes with PBS-Tween 20, the plates were blocked for two hours with 200 microliters/well of blocking buffer. After 4 washes, 50 microliters/well of human sera diluted 1:100 in blocking buffer were added to duplicate wells and incubated for 1 hour. The plates were washed four times and 50 microliters/well of peroxidase-conjugated goat anti-human IgG or IgM (heavy chain-specific, Jackson ImmunoResearch Laboratories, Inc.), diluted 1:1000 in blocking buffer were added and incubated for 1 hour. After 4 washes, 50 microliters/well of 0.8 mg/ml o-phenylenediamine in 0.1 M citrate buffer, pH 6, with 0.003% hydrogen peroxide were added to each well and the plates developed for 10 minutes. The plates were read at 492 nm using an ELISA reader. The cut-off value for positivity was the 97.5th percentile relative to normal controls ($OD_{492} \geq 0.11$ for IgG and $OD_{492} \geq 0.22$ for IgM). The frequencies of anti-b2gpI of IgG and IgM isotype in our SLE population were 33% and 18%, respectively. The frequency of any anti-b2gpI (IgG and/or IgM) was 39.4%. In our normal population, the frequencies were: IgG anti-b2gpI 3.3%; IgM anti-b2gpI 6.5%; and any anti-b2gpI 9.8%.

αCL Antibodies

The assay was performed by ELISA as previously described (14). A cut-off point greater than the mean $OD_{405}$ value plus 2 standard deviations in 60 normal controls was selected ($OD_{405} \geq 0.81$ for IgG aCL and $\geq 0.73$ for IgM aCL). The frequencies of aCL of IgG and IgM isotypes in our SLE population were 36.2% and 8.5%, respectively. The frequency of any aCL (IgG and/or IgM) was 40.4%. In our normal population, the frequencies were: IgG aCL, 8.3%; IgM aCL, 5%; and any aCL, 11.6%. Plasma samples from the patients (seen between Apr. 1983 and Dec. 1992) were considered to have LA activity if it prolonged the activated partial thromboplastin time (aPTT) by at least 8 seconds (compared to the normal plasma control), and the prolongation was not corrected by a 1:1 dilution with normal plasma. LA was considered to be positive if present on at least two occasions at a minimum of 3 months apart.

Statistical Analysis $X^2$ analysis with Yate's correction was performed for frequency comparison among groups (using two-tailed Fisher's exact test, where applicable) and the t test for comparison of group means using InStat software (GraphPad Software Inc., San Diego, Calif.). P values less than or equal to 0.05 were considered statistically significant. In order to correct for multiple testing, Bonferroni correction was used. Associations between anti-lamin B1 autoantibodies and SLE manifestations were analyzed by stepwise multiple logistic regression, using SPSS software.

RESULTS

Frequency of IgG Anti-Lamin B1 Autoantibodies

Figure 2:
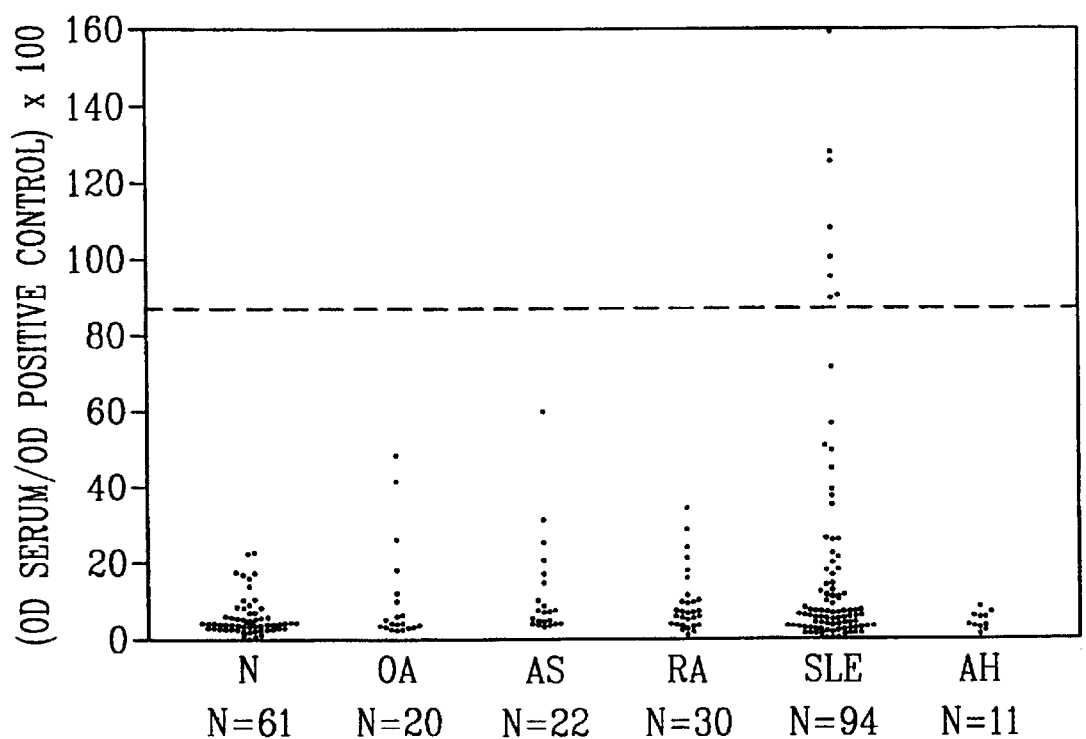
FIG. 2 illustrates distribution of IgG anti-lamin B1 autoantibodies in SLE patients versus normal and disease controls.

FIG. 2 is a scattergram showing the distribution of IgG anti-lamin B1 autoantibodies in SLE versus various control groups. At a cut-off point of 88% (dotted line), corresponding to 16 SD above the mean value in normal controls, anti-lamin B1 autoantibodies were strikingly restricted to a subset of SLE patients. The mean anti-lamin B1 antibody activity in the latter subset (n=8) was highly significantly greater than in the other SLE patients (n=86) (P<0.001) or in any control group (P<0.001). NL, normal; OA, osteoarthritis; AS, ankylosing spondylitis; AH, autoimmune hepatitis.

A high level (>87%) of IgG anti-lamin B1 autoantibodies, corresponding to 16 SD above the mean in normal controls, was strikingly restricted to a subset of 8 (8.5%) SLE patients. These sera also expressed high titers of anti-lamin B1 activity by immunoblotting (data not shown). Comparison of the mean IgG anti-lamin B1 levels in this SLE subset (n=8), the other SLE patients (n=86) and the control groups revealed a highly significant difference (P<0.001, by Kruskal-Wallis non-parametric analysis of variance).

Clinical Associations of IgG Anti-Lamin B1 Autoantibodies in SLE by Univariate Analysis The incidence of 57 SLE clinical and laboratory manifestations was systematically compared by univariate analysis in the patient subset positive for IgG anti-lamin B1 autoantibodies (OD 16 SD above the normal controls, n=8) versus patients negative for IgG anti-lamin B1 autoantibodies (OD<16 SD, n=86). Results are shown in Table 2. In patients positive for IgG anti-lamin B1 autoantibodies, there was a striking and significantly greater frequency of LA (100% versus 18.6%, odds ratio [OR] 72.6, 95% confidence interval [95% CI] 3.98 to 1323.8, P=0.00001). Other manifestations associated with IgG anti-lamin B1 autoantibodies were: thrombocytopenia (OR 6.7, 95% CI 1.46 to 31.14, P=0.016), IgG anti-b2gpI autoantibodies (OR 7.32, 95% CI 1.38 to 38.77, P=0.014) and IgM anti-b2gpI autoantibodies (OR 5.61, 95% CI 1.24 to 25.33, P=0.033). After Bonferroni correction, only the association with LA remained strongly significant (Table 2).

TABLE 2

Univariate analysis of IgG anti-lamin B1 autoantibody associations in 94 SLE patients

| Single manifestations | Positive IgG anti-lamin B1 n = 8 | | Negative IgG anti-lamin B1 n = 86 | | 95% Confidence Interval | Odds Ratio | P |
|---|---|---|---|---|---|---|---|
| | n | % | n | % | | | |
| LA | 8 | 100.0 | 16 | 18.6 | 3.98 to 1323.8 | 72.6 | .00001* |
| Thrombocytopenia | 5 | 62.5 | 17 | 19.8 | 146 to 31.14 | 6.7 | .016 |

TABLE 2-continued

Univariate analysis of IgG anti-lamin B1 autoantibody associations in 94 SLE patients

| Single manifestations | Positive IgG anti-lamin B1 n = 8 | | Negative IgG anti-lamin B1 n = 86 | | 95% Confidence Interval | Odds Ratio | P |
|---|---|---|---|---|---|---|---|
| | n | % | n | % | | | |
| Anti-b2gpI IgG | 6 | 75.0 | 25 | 29.1 | 1.38 to 38.77 | 7.3 | .014 |
| Anti-b2gpI IgM | 4 | 50.0 | 13 | 15.1 | 1.24 to 25.33 | 5.6 | .033 |
| ACL IgG | 5 | 62.5 | 29 | 33.7 | 0.73 to 14.68 | 3.2 | NS |
| ACL IgM | 2 | 25 | 6 | 7.0 | 0.73 to 26.96 | 4.4 | NS |
| ACL any | 6 | 75.0 | 32 | 37.2 | 0.96 to 26.60 | 5.0 | .058 |
| Neutropenia | 6 | 75.0 | 45 | 52 | 0.52 to 14.31 | 2.7 | NS |
| Lymphopenia | 7 | 87.5 | 50 | 58 | 0.59 to 42.80 | 5.0 | NS |
| Positive Coombs' test | 3 | 37.5 | 13 | 15 | 0.71 to 15.85 | 3.3 | NS |

LA: lupus anticoagulant antibodies; anti-b2gpI: anti-b2-glycoprotein I antibodies; aCL IgG; aCL IgM; aCL any: anti-cardiolipin antibodies of IgG and/or IgM isotype(s).
*P value is still significant after Bonferroni correction for multiple comparisons.

Interestingly, neutropenia, lymphopenia, a positive Coombs' test, and aCL of IgG and/or IgM isotypes were more common in patients with anti-lamin B1, but this was not significant (Table 2).

IgG anti-lamin B1 autoantibodies were strikingly linked with LA, thrombocytopenia, aCL and anti-b2gpI, when these manifestations were associated. Thus, a significantly greater proportion of patients with IgG anti-lamin B1 expressed the double association of LA and thrombocytopenia than patients without anti-lamin B1 (OR 18.8, 95% CI 3.69 to 95.72, P=0.0007). The triple association of LA, IgG anti-b2gpI and IgG aCL (OR 20.5, 95% CI 3.7 to 113.52, P=0.0014) and the quadruple association of LA, anti-b2gpI, IgG aCL and thrombocytopenia (OR 25.2, 95% CI 3.39 to 187.01, P=0.004) were significantly more common in patients with IgG anti-lamin B1 than those without anti-lamin B1.

Multiple Regression Analysis

Stepwise multiple logistic regression was used to identify variable(s) best associated with IgG anti-lamin B1 autoantibodies. The variables entered included potentially confounding variables such as age, sex, and disease duration at first serum, and prednisone use before and at the time the first serum was obtained. The variable that was most associated with IgG anti-lamin B1 was LA (P<0.00001). The other associated variables were lymphopenia, aCL of IgG and/or IgM isotypes and neutropenia. Because of the extremely strong association between IgG anti-lamin B1 and LA, analysis was repeated after deletion of the LA variable from the model in order to detect other potential associations. This revealed that IgG anti-b2gpI (P=0.019) and lymphopenia (P=0.043) were also associated with IgG anti-lamin B1.

Stepwise multiple logistic regression analysis was also performed to determine which SLE manifestations were most strongly associated with the presence of LA. The variable most associated with LA was the presence of IgG anti-lamin B1 autoantibodies (P<0.00001). Other associated variables were thrombocytopenia (P=0.0032) and anti-b2gpI of IgG and/or IgM isotypes (P=0.044).

Influence of IgG Anti-Lamin B1 on the Frequency of Thrombotic Manifestations Since LA are known to be associated with the thrombotic manifestations of the anti-phospholipid syndrome, we determined whether this association also occurred in our 94 SLE patients during their disease course. The presence of LA at first evaluation was indeed associated with thrombosis (OR 3.17, 95% CI 1.41 to 9.54, P=0.024) As IgG anti-lamin B1 autoantibodies were strongly associated with LA in these patients, we determined whether these autoantibodies also associated with thrombosis. In striking contrast to LA, this was not the case (OR 1.18, 95% CI 0.26 to 5.28, P=1.0). We then studied the effect of IgG anti-lamin B1 autoantibodies on the frequency of thrombosis in patients with LA. As shown in Table 3, the frequency of thrombosis was not significantly different in patients expressing both LA and IgG anti-lamin B1 in comparison with other SLE patients (OR 1.179, 95% CI 0.26 to 5.28, P=1.0) . However, patients expressing LA without IgG anti-lamin B1 had a significantly greater frequency of thrombosis in comparison with other SLE patients (OR 4.24, 95% CI 1.37 to 13.08, P=0.018) (Table 3).

TABLE 3

Effect of IgG anti-lamin B1 autoantibodies on frequency of thrombosis in SLE patients with lupus anticoagulant antibodies

| | Thrombosis n | No thrombosis n | |
|---|---|---|---|
| Presence of LA and IgG anti-lamin B1 | 3 | 5 | Odds Ratio 1.179 95% CI 0.263 to 5.285 |
| All other patients | 29 | 57 | P = 1.0 |
| Presence of LA and absence of IgG anti-lamin B1 | 10 | 6 | Odds Ratio 4.242 95% CI 1.376 to 13.083 |
| All other patients | 22 | 56 | P = .018 |

LA: lupus anticoagulant antibodies.

This frequency was not due to a longer disease duration in the latter group compared to the former group (mean duration 2687 SD 1534 days, versus 3148 SD 2110 days, respectively, P=0.32 by 2-tail t test). Similarly, no significant difference in disease duration was present between SLE patients with both LA and IgG anti-lamin B1 compared to those with LA without IgG anti-lamin B1 (mean duration 3134 SD 1046 days, versus 2687 SD 1534, P=0.41).

Isotypes of Anti-Lamin B1 Autoantibodies

The frequency of IgM and IgA anti-lamin B1 was studied by ELISA in sera from the 8 patients with high titers of IgG anti-lamin B1 autoantibodies. Four patients expressed IgG anti-lamin B1 only. Coexpression of IgG plus IgM plus IgA (n=2), IgG plus IgM (n=1) or IgG plus IgA (n=1) anti-lamin B1 was observed in the remaining 4 patients. In all instances, IgG was the dominant isotype. In the 6 patients with high titers of IgG anti-lamin B1 and aCL of IgG and/or IgM isotypes, isotypes of aCL were IgG only (n=4), IgM only (n=1) and IgG plus IgM (n=1).

Expression of Other Antinuclear Autoantibodies (ANAs) in Patients With Anti-Lamin B1 Autoantibodies To determine whether anti-lamin B1 autoantibodies are expressed alone or in association with other ANAs, we used ELISAs for antibodies to Ro, La, Sm and U1RNP antigens, and filter-binding assay for anti-native DNA antibodies as previously described. Antibodies to Ro, La and/or U1RNP antigens were detected in 4 of 8 patients (anti-Ro, anti-Ro and La, anti-Ro and U1RNP, anti-U1RNP, respectively). No statistical association was noted between these ANAs and anti-lamin B1 antibodies. Anti-native DNA antibodies were absent from the 8 index sera (the mean DNA-binding value was 13% SD 7.1%, range 4% to 28%, normal <30%).

DISCUSSION

We have shown that high titers of IgG anti-lamin B1 autoantibodies are highly restricted to a subset of patients with SLE. This subset accounts for 8.5% of our SLE population. We and others have previously shown that anti-lamin B antibodies in low titers may be present in sera from normal adults and from patients with various inflammatory and noninflammatory disease controls. In the present study, using rigorously defined unselected and consecutive controls and SLE patients, high titers of IgG anti-lamin B1 autoantibodies were not observed in any normal or disease control subject.

LA are known to be strongly associated with the thrombotic manifestations of the anti-phospholipid syndrome. Our data show that IgG anti-lamin B1autoantibodies are associated with a particular clinical subset of SLE patients, characterized by the presence of LA apparently with a lesser risk for thrombosis. However, this LA and anti-lamin B1 group was small and this must be confirmed with larger numbers of patients. This subset accounts for 33.3% of our LA-positive SLE population. This is in marked contrast with the significantly increased frequency of thrombotic events in our SLE patients with LA but without IgG anti-lamin B1 autoantibodies. These data suggest that quantitation of IgG anti-lamin B1autoantibodies may be useful in the prognostic assessment of thrombotic risk in SLE patients with LA. Studies are now underway in our laboratory to verify this hypothesis in a large number of SLE patients from other cohorts.

By stepwise multiple logistic regression, LA was the variable most associated with IgG anti-lamin B1 autoantibodies and the reverse was true as well, as the SLE manifestation most associated with LA was the presence of high titers of IgG anti-lamin B1 autoantibodies. All patients with IgG anti-lamin B1 autoantibodies expressed LA. However, 66% of our patients with LA did not express IgG anti-lamin B1 autoantibodies. Taken altogether, these data strongly suggest that a subset of LA are linked to IgG anti-lamin B1 autoantibodies. This subset of LA may be cross-reactive with anti-lamin B1 autoantibodies and does not appear to share the prothrombotic pathogenicity characteristic of LA that are not associated with anti-lamin B1 autoantibodies. In contrast, LA associated with thrombosis are neither linked nor cross-reactive with anti-lamin B1 and so, may have different antigen-binding specificities. Research is currently underway in our laboratories to explore this possibility.

Interestingly, IgG anti-lamin B1 autoantibodies were more frequently associated with a cluster of manifestations, such as thrombocytopenia, anti-b2gpI IgG or IgM antibodies and a positive Coombs' test. This cluster encompasses manifestations that are characteristic of the anti-phospholipid syndrome. However, these associations lost statistical significance when multiple logistic regression and the Bonferroni correction were used (Table 2). Since LA was the variable most associated with IgG anti-lamin B1 autoantibodies, this suggests that this cluster of other variables, noted by us and by others, is tightly related, but secondary, to the LA/anti-lamin B1 association.

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth, and as follows in the scope of the appended claims.

What is claimed is:

1. A method to determine predisposition to thrombosis in a patient with SLE, which comprises the step of:

determining the presence or absence of anti-lamin B1 (aLB1) antibodies in a biological sample of said patient;

determining the presence or absence of lupus anticoagulant (LA) antibodies in said biological sample;

wherein presence of aLB1 antibodies with or without LA antibodies is indicative of a low risk of thrombosis incidence; and wherein presence of LA antibodies with absence of aLB1 antibodies is indicative of a predisposition to thrombosis.

2. The method of claim 1, wherein said sample is a serum sample.

3. The method of claim 2, wherein the step of determining is effected with LA and LB1 antigen.

* * * * *